(12) United States Patent
Dong et al.

(10) Patent No.: US 11,173,105 B2
(45) Date of Patent: *Nov. 16, 2021

(54) ORAL CARE COMPOSITIONS AND METHODS FOR THE SAME

(71) Applicant: Colgate-Palmolive Company, New York, NY (US)

(72) Inventors: Rong Dong, Highland Park, NJ (US); Irene Petrou, Parsippany, NJ (US); Paloma Pimenta, Staten Island, NY (US); Stacey Lavender, Chesterfield, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/161,162

(22) Filed: Oct. 16, 2018

(65) Prior Publication Data

US 2020/0113808 A1    Apr. 16, 2020

(51) Int. Cl.

| | | |
|---|---|---|
| *A61K 8/81* | (2006.01) | |
| *A61K 8/21* | (2006.01) | |
| *A61Q 11/00* | (2006.01) | |
| *A61K 8/9767* | (2017.01) | |
| *A61K 8/73* | (2006.01) | |
| *A61K 8/36* | (2006.01) | |
| *A61K 8/02* | (2006.01) | |

(52) U.S. Cl.
CPC .......... *A61K 8/8158* (2013.01); *A61K 8/0204* (2013.01); *A61K 8/361* (2013.01); *A61K 8/731* (2013.01); *A61K 8/8152* (2013.01); *A61K 8/9767* (2017.08); *A61Q 11/00* (2013.01)

(58) Field of Classification Search
None
See application file for complete search history.

(56) References Cited

U.S. PATENT DOCUMENTS

| | | |
|---|---|---|
| 7,252,836 B2 | 8/2007 | Brown et al. |
| 8,883,212 B2 | 11/2014 | Pillai et al. |
| 9,808,416 B2 | 11/2017 | Georges et al. |
| 2005/0281757 A1 | 12/2005 | Ibrahim et al. |
| 2007/0196323 A1 | 8/2007 | Zhang et al. |
| 2014/0242001 A1* | 8/2014 | Pillai .................. A61P 21/02 424/52 |
| 2016/0074290 A1 | 3/2016 | Sagel et al. |
| 2016/0220472 A1 | 8/2016 | Wang et al. |
| 2017/0128346 A1* | 5/2017 | Dong ................ A61K 8/8158 |
| 2018/0168982 A1* | 6/2018 | Yuan .................. A61K 8/86 |
| 2018/0193247 A1 | 7/2018 | Dong et al. |

OTHER PUBLICATIONS

International Search Report and the Written Opinion of the International Searching Authority issued in international application PCT/US2018/055972 dated Feb. 12, 2019.

* cited by examiner

*Primary Examiner* — Brian Gulledge

(57) ABSTRACT

Film forming compositions and methods for occluding dentin tubules of teeth to treat dentinal hypersensitivity of the teeth are provided. The film forming compositions may include a hydrophobic copolymer, a rosin, and an orally acceptable solvent. The hydrophobic copolymer may include an acrylate/octylacrylamide copolymer, such as 2-propenoic acid, 2-methyl-, 2-methylpropyl ester, polymer with 2-propenoic acid and N-(1,1,3,3-tetramethylbutyl)-2-propenamide. Methods for treating dentinal hypersensitivity may include contacting the film forming composition with surfaces of the teeth.

13 Claims, No Drawings

ORAL CARE COMPOSITIONS AND METHODS FOR THE SAME

BACKGROUND

Dentin or dentinal hypersensitivity is a common clinical condition associated with exposed dentin surfaces of teeth. Dentin contains a large numbers of pores or dentin tubules that extend from outer surfaces of the teeth to nerves within the teeth. As such, exposure of the dentin often leads to increased sensitivity of the teeth to external stimuli (e.g., temperature, pressure, etc.). In view of the foregoing, conventional oral care products or compositions thereof may often attempt to numb the nerve or incorporate filling or occluding agents to ameliorate the sensitivity of the teeth. For example, conventional oral care compositions may incorporate filling or occluding agents to physically block or fill the dentin tubules, thereby shielding the nerve from the external stimuli. These conventional methods, however, may often require treatment for several days or weeks before any appreciable reduction or improvement in sensitivity is observed. Further, conventional methods may utilize occluding agents in dentifrices (e.g., toothpastes), which may rinse of throughout the day, thereby reducing the effectiveness.

What is needed, then, are improved desensitizing oral care products and compositions, and methods for reducing dental sensitivity and/or dentin hypersensitivity.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a film forming composition for occluding dentin tubules of teeth. The film forming composition may include a hydrophobic copolymer, a rosin, and an orally acceptable solvent.

In at least one implementation, the hydrophobic copolymer may include an acrylate. The hydrophobic polymer may be or include an acrylate/octylacrylamide copolymer. The acrylate/octylacrylamide copolymer may be 2-propenoic acid, 2-methyl-, 2-methylpropyl ester, polymer with 2-propenoic acid and N-(1,1,3,3-tetramethylbutyl)-2-propenamide. The hydrophobic copolymer may also include at least one of octylacrylamide/acrylates/butylaminoethyl methacrylate copolymer, VA/butyl maleate/isobornyl acrylate copolymer, acrylates/T-butylacrylamide copolymer, polyvinylpyrrolidone/vinyl acetate copolymer, triacontanyl PVP copolymer, acrylates/dimethylaminoethyl methacrylate copolymer, or mixtures thereof.

In at least one implementation, the film forming composition may further include one or more desensitizing agents with various modes of action. The desensitization agents could physically occlude, depolarize the nerve, and/or provide an analgesic effects to reduce pain. The desensitizing agents may include one or more of a potassium salt, arginine, participated calcium carbonate, small particle silicas, eugenol, strontium salts, zinc salts, chloride salts, and mixtures or combinations thereof.

In at least one implementation, the orally acceptable solvent may include one or more of ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, and benzyl alcohol. In a preferred implementation, the orally acceptable solvent includes ethanol.

In at least one implementation, the film forming composition may include an adhesive. In at least one implementation, the adhesive may include one or more of a polyvinyl acetaldehyde, a polyvinyl alcohol, a polyvinyl acetate, a poly(ethylene oxide), a polyacrylate, a polyvinylpyrolidone, a polyvinylpyrolidone/vinyl acetate copolymer, a polyoxyethylene/polyoxopropylene block copolymer, a silicone resin, and combinations thereof.

In at least one implementation, the film forming composition may include a cellulose derivative. The cellulose derivative may include an alkyl cellulose ether. In a preferred implementation, the cellulose derivative may include ethyl cellulose.

In at least one implementation, the cellulose derivative is the ethyl cellulose, and the ethyl cellulose includes an average substitution value of about 2.25 to about 2.60 ethoxyl groups per anhydroglucose unit.

In at least one implementation, the film forming composition may further include one or more fatty acids, optionally, the fatty acids is oleic acid.

In at least one implementation, the rosin is at least partially hydrogenated. In another implementation, the rosin is fully hydrogenated.

The foregoing and/or other aspects and utilities embodied in the present disclosure may be achieved by providing a method for at least partially occluding dentin tubules of teeth in a subject. The method may include contacting any one of the film forming composition disclosed herein with the teeth of the subject in need thereof.

The foregoing and/or other aspects and utilities embodied in the present disclosure may be achieved by providing a method for reducing dental sensitivity of teeth of a subject. The method may include applying any one of the film forming composition disclosed herein with the teeth of the subject in need thereof.

In at least one implementation, the method may further include treating the teeth with a toothpaste. In another implementation, the film forming composition may be applied after treating the teeth with the toothpaste.

The foregoing and/or other aspects and utilities embodied in the present disclosure may be achieved by providing a method for preparing any one of the film forming compositions disclosed herein. The method may include contacting the hydrophobic copolymer, the rosin, and the orally acceptable solvent with one another.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that applying a film forming composition including a hydrophobic polymer (e.g., a acrylate/octylacrylamide copolymer) and/or a rosin to surfaces of teeth enhances the occlusion of dentin tubules thereof. The present inventors have also surprisingly and unexpectedly discovered that applying the film forming composition including the hydrophobic polymer and/or the rosin after treatment with a toothpaste for sensitivity maintains, enhances, and/or facilitates the occlusion of dentin tubules, even after an acid challenge.

Compositions

Compositions disclosed herein may be or include an oral care product or a film forming composition thereof. For example, the compositions disclosed herein may be an oral care product including the film forming composition, or the film forming composition thereof. In at least one implementation, the film forming composition may include one or more hydrophobic polymers and/or one or more rosins. For example, the film forming composition may include an acrylate/octylacrylamide copolymer and/or a rosin, such as an at least partially hydrogenated rosin. As further described herein, the film forming compositions and/or one or more components thereof may be capable of or configured to enhance, facilitate, and/or maintain occlusion of dentin tubules of teeth when applied to surfaces thereof. For example, the film forming compositions and/or one or more components thereof may be configured to at least partially occlude the dentin tubules of teeth to reduce the sensitivity of the teeth. The film forming compositions disclosed herein may also be configured to enhance, facilitate, and/or maintain the occlusion of the dentin tubules treated with a toothpaste. For example, the film forming compositions disclosed herein may be applied prior to, along with, and/or after treatment with a toothpaste to enhance, facilitate, and/or maintain the ability of the toothpaste to occlude dentin tubules.

Hydrophobic Polymers

The one or more hydrophobic polymers of the film forming composition may be or include, but are not limited to, hydrophobic film forming polymers, such as hydrophobic film forming polymers having functional groups with properties that provide relatively increased adhesion to surfaces of the oral cavity (e.g., surfaces of teeth). Illustrative functional groups may include, but are not limited to, carboxyl groups, phosphate groups, hydroxyl groups, amines, disulfides, nitro groups, or the like, and combinations thereof.

In at least one implementation, the hydrophobic polymer may be or include a copolymer. For example, the hydrophobic polymer may be or include a carboxylated acrylic copolymer. In another example, the hydrophobic polymer may be a copolymer of octylacrylamide and one or more monomers, where the one or more monomers may include one or more of acrylic acid, methacrylic acid, and any one or more simple esters thereof. In yet another example, the hydrophobic polymer may be a polymer formed from octylacrylamide, t-butylaminoethyl methacrylate, and one or more monomers of acrylic acid, methacrylic acid, or any one or more simple esters thereof. Illustrative carboxylated acrylic copolymers may be or include, but are not limited to, those sold under the trade names DERMACRYL®, AMPHOMER®, BALANCE®, and VERSACRYL®, which are commercially available from AkzoNobel Company, Surface Chemistry of Amsterdam, Netherlands. For example, the carboxylated acrylic copolymers may be or include, but are not limited to, AMPHOMER® 4961, AMPHOMER® HC, DERMACRYL® 2.0, RESYN™ XP, a hydrophobic copolymer selected from octylacrylamide/acrylates/butylaminoethyl methacrylate copolymer, such as AMPHOMER® LV-71, AMPHOMER®, AMPHOMER® EDGE™, BALANCE® 47, or the like, and combinations thereof, all of which are commercially available from AkzoNobel Company, Surface Chemistry of Amsterdam, Netherlands. The hydrophobic copolymer may be selected from VA/butyl maleate/isobornyl acrylate copolymer, such as ADVANTAGE™ PLUS from Ashland Global Specialty Chemicals Inc. of Covington, Ky. The hydrophobic copolymer may be selected from acrylates/t-butylacrylamide copolymer, such as ULTRAHOLD® STRONG and ULTRAHOLD® 8 from BASF SE of Ludwigshafen, Germany. The hydrophobic copolymer may be selected from acrylates/dimethylaminoethyl methacrylate copolymer, such as the EUDRAGIT® range of polymers from Evonik Industries of Essen, Germany, such as EUDRAGIT® E100, EUDRAGIT® E PO, EUDRAGIT® RS 100, EUDRAGIT® RS PO, EUDRAGIT® RL PO, EUDRAGIT® RL 100, or the like, and combinations thereof. The hydrophobic copolymer may be selected from polyvinylpyrrolidone/vinyl acetate, such as the PVP/VA series of polymers from Ashland Global Specialty Chemicals Inc. of Covington, Ky. The hydrophobic copolymer may be selected from triacontanyl PVP, such as GANEX™ WP-660 from Ashland Global Specialty Chemicals Inc. of Covington, Ky. The hydrophobic copolymer may be selected from at least one of octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, or mixtures thereof. In an preferred implementation, the hydrophobic polymer may be a copolymer of 2-Propenoic acid, 2-methyl-, 2-methylpropyl ester, polymer with 2-propenoic acid and N-(1,1,3,3-tetramethylbutyl)-2-propenamide or 2-propenoic acid, 2-methyl-, 2-methylpropyl ester, 2-propenoic acid, N-(1,1,3,3-tetramethylbutyl)-2-propenamide copolymer (CAS 129702-02-9). For example, the hydrophobic polymer may be or include, but is not limited to, DERMACRYL® 79, which is commercially available from AkzoNobel Company, Surface Chemistry of Amsterdam, Netherlands.

The amount or concentration of the one or more hydrophobic polymers present in the oral care product or the film forming composition thereof may vary widely. In at least one implementation, the amount of the one or more hydrophobic polymers present may be from about 1 weight % to about 50 weight %, based on a total weight of the oral care product or the film forming composition thereof. For example, the amount of the one or more hydrophobic polymers present may be from about 1 weight %, about 5 weight %, about 10 weight %, about 15 weight %, about 20 weight %, or about 25 weight % to about 30 weight %, about 35 weight %, about 40 weight %, about 45 weight %, or about 50 weight %. In another example, the amount of the one or more hydrophobic polymers present may be from about 1 weight % to about 50 weight %, about 5 weight % to about 45 weight %, about 10 weight % to about 40 weight %, about 15 weight % to about 35 weight %, about 20 weight % to about 30 weight %, or about 22.5 to about 28.5, or about 25 weight %. In at least one implementation, the amount of the one or more hydrophobic polymers present may be from about 10 weight % to about 30 weight %, based on a total weight of the oral care product or the film forming composition thereof. For example, the amount of the one or more hydrophobic polymers present may be from about 10 weight %, about 12 weight %, about 14 weight %, about 16 weight %, about 18 weight %, about 19 weight %, or about 19.5 weight % to about 20.5 weight %, about 21 weight %, about 22 weight %, about 24 weight %, about 26 weight %, about 28 weight %, or about 30 weight %, based on a total weight of the oral care product or the film forming composition thereof. In another example, the amount of the one or more hydrophobic polymers present may be from about 10 weight % to about 30 weight %, about 12 weight % to about 28 weight %, about 14 weight % to about 26 weight %, about 16 weight % to about 24 weight %, about 18 weight % to about 22 weight %, about 19 weight % to about 21 weight %, or about 19.5 weight % to about 20.5 weight %, based on a total weight of the oral care product or the film forming composition thereof. In a preferred implementation, the amount of the one or more hydrophobic polymers present may be from about 19 weight % to about 21 weight %, about 19.5 weight % to about 20.5 weight %, or about 20 weight %, based on a total weight of the oral care product or the film forming composition thereof.

Desensitizing Agents

The oral care product or the film forming composition thereof may include one or more desensitizing agents. Illustrative desensitizing agents may be or include, but are not limited to, potassium salts (e.g., potassium nitrate, potassium bicarbonate, potassium chloride, potassium citrate, potassium oxalate, etc.); arginine, other occluding agents, such as calcium carbonate, and/or other small particle occlusive agents such as amorphous silicas, camphor, eugenol; strontium salts; zinc salts, AC43; chloride salts, and the like, and mixtures or combinations thereof.

The amount or concentration of the one or more desensitizing agents present in the oral care product or the film forming composition thereof may vary widely. In at least one implementation, the desensitizing agents may be presented in an effective amount to at least partially reduce or maintain sensitivity of teeth. For example, the desensitizing agent may be present in an amount of from about 0.01 weight % to about 20 weight %, based on a total weigh of the oral care composition or the film forming composition thereof. For example, the desensitizing agent may be present in an amount of from about 0.01 weight %, about 1 weight %, about 2 weight %, about 4 weight %, about 6 weight %, about 8 weight %, or about 10 weight % to about 12 weight %, about 14 weight %, about 16 weight %, about 18 weight %, or about 20 weight %, based on a total weigh of the oral care composition or the film forming composition thereof.

Rosin

The oral care product or the film forming composition thereof may include one or more rosins. In at least one implementation, the one or more rosins may be at least partially hydrogenated. The one or more rosins may be completely or fully hydrogenated. Hydrogenated rosins may be rosin acids or resin acids that have at least some of their carbon-carbon double bonds hydrogenated. It should be appreciated that the relatively greater degree in which the rosins are hydrogenated, the more colorless they appear to the human eye. Accordingly, in at least one implementation, the oral care product or the film forming composition thereof may include a fully hydrogenated rosin that may be transparent or substantially transparent.

Illustrative rosins may be or include, but are not limited to, rosins from the class of rosins known in the art as the colophonium class. Members of the colophonium class are non-synthetic naturally-derived sticky resins (e.g., typically derived from various species of pine). Colophonium may include a substantial fraction of resin acid components that are isomeric with abietic acid ($C_{20}H_{30}O_2$). Examples of colophonium may also include dihydrobietic acid ($C_{20}H_{32}O_2$) and/or dehydroabietic acid ($C_{20}H_{28}O_2$). Colophonium may range from black to substantially colorless, although resins from this class may typically be pale yellow to amber in color and have a density of about 1.07 to about 1.09 $g/cm^3$. Various materials that are individually referred to as "colophonium" include Canadian balsam, Olibanum balsam, Elemi resin, Opopanax resin, Tolu balsam, Peruvian balsam, and POLY-PALE™ resin, which is a partially dimerized rosin commercially available from Eastman Chemical Company of Kingsport, Tenn. Illustrative rosins may also be or include, but are not limited to, wood rosin, gum rosin, tall oil rosin and mixtures thereof. The rosins may be in a crude state or a refined state.

In a preferred implementation the one or more rosins of the film forming composition, when present, may be or include, but is not limited to, FORAL™ AX-E, a fully hydrogenated tree rosin that has been distilled and dimerized, which is commercially available from Eastman Chemical Company. FORAL™ AX-E is nearly colorless and in some implementations is more stable than colophonium components. FORAL™ AX-E resists oxidation and retains its substantially colorless characteristics over time. Other suitable commercially available rosins include STAY-BELITE™ Resin-E, a partially hydrogenated rosin available from Eastman Chemical Company, which also exhibits good oxidation resistance and pale color. Additional suitable commercially available rosins include PAMITE™ (tall oil rosin), DYMEREX™ (dimerized rosin), POLYSTIX® 90 (partially dimerized rosin), DRESINATE™ (rosin soap) and PERMALYN™ NC-11 (noncrystalline rosin), all of which are commercially available from Eastman Chemical Company.

The amount or concentration of the one or more rosins present in the oral care product or the film forming composition thereof may vary widely. In at least one implementation, the amount of the rosins present in the film forming composition may be from about 1 weight % to about 9 weight %, based on a total weight of the oral care product or the film forming composition thereof. For example, the amount of the rosins present in the film forming composition may be from about 1 weight %, about 2 weight %, about 3 weight %, about 4 weight %, or about 4.5 weight % to about 5.5 weight %, about 6 weight %, about 7 weight %, about 8 weight %, or about 9 weight %, based on a total weight of the oral care product or the film forming composition thereof. In another example, the amount of the rosins present in the film forming composition may be from about 1 weight % to about 9 weight %, about 2 weight % to about 8 weight %, about 3 weight % to about 7 weight %, about 4 weight % to about 6 weight %, or about 4.5 weight % to about 5.5 weight %. In a preferred implementation, the amount of the rosins present may be from about 4 weight % to about 6 weight %, about 4.5 weight % to about 5.5 weight %, or more preferably about 5 weight %.

Derivative of Cellulose

The oral care product or the film forming composition thereof may include one or more derivatives of cellulose or cellulose derivatives. The cellulose derivatives may be or include, but is not limited to, an alkyl cellulose ether. As used herein, the expression "alkyl cellulose ether" may refer to a lower alkyl ether of cellulose, such as an ethyl cellulose. In a preferred implementation, the cellulose derivative is ethyl cellulose. The degree of ethoxylation and/or the viscosity of the ethyl cellulose may vary. For example, the ethyl cellulose may have a degree of ethoxylation of about 45% to about 50% and a viscosity of about 3 cP to about 70 cP (5% solution at 25° C. measured in a Ubbelohde viscometer). In another example, the ethyl cellulose may have an average substitution value of about 2.25 to about 2.60 ethoxyl groups per anhydroglucose unit, or about 44% to about 52% ethoxyl content. In yet another example, the ethyl cellulose may have an average substitution value of about 2.46 to about 2.58 ethoxyl groups per anhydroglucose unit, corresponding to an ethoxyl content of about 48% to about 49.5%. Illustrative ethyl celluloses may be or include, but are not limited to, AQUALON® N100 ethyl cellulose, commercially available from Hercules Inc. of Wilmington, Del., ETHOCEL® Standard 100, ETHOCEL™ E7, ETHOCEL™ E22, ETHOCEL™ E50, or the like, and mixtures thereof, all of which are commercially available from the Dow Corning Company.

The amount or concentration of the cellulose derivatives present in the oral care product or the film forming composition thereof may vary widely. In at least one implementation, the amount of the cellulose derivatives present in the film forming composition may be from about 0.01 weight % to about 50 weight %, based on a total weight of the oral care product or the film forming composition thereof. For example, the amount of the cellulose derivatives present in the film forming composition may be from about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 5 weight %, about 10 weight %, about 15 weight %, about 20 weight %, or about 25 weight % to about 30 weight %, about 35 weight %, about 40 weight %, about 45 weight %, or about 50 weight %. In another example, the amount of the cellulose derivative present may be from about 0.01 weight %, about 0.1 weight %, about 0.2 weight %, about 0.3 weight %, about 0.4 weight %, about 0.5 weight %, about 0.6 weight %, about 0.7 weight %, or about 0.8 weight % to about 0.9 weight %, about 1 weight %, about 1.1 weight %, about 1.2 weight %, about 1.3 weight %, about 1.4 weight %, about 1.5 weight %, about 1.6 weight %, or about 1.7 weight %. In another example, the amount of the cellulose derivatives present in the film forming composition may be from about 1 weight % to about 50 weight %, about 5 weight % to about 45 weight %, about 10 weight % to about 40 weight %, about 15 weight % to about 35 weight %, about 20 weight % to about 30 weight %, or about 22.5 to about 28.5, or about 25 weight %. In another implementation, the amount of the cellulose derivatives present in the film forming composition may be from about 10 weight % to about 16 weight %. For example, the amount of the cellulose derivatives present in the film forming composition may be from about 10 weight %, about 11 weight %, about 12 weight %, or about 12.5 weight % to about 13.5 weight %, about 14 weight %, about 15 weight %, or about 16 weight %, based on a total weight of the oral care product or the film forming composition thereof. In another example, the amount of the cellulose derivatives present in the film forming composition may be from about 10 weight % to about 16 weight %, about 11 weight % to about 15 weight %, about 12 weight % to about 14 weight %, or about 12.5 weight % to about 13.5 weight %. In a preferred implementation, the amount of the cellulose derivative, such as ethyl cellulose, present in the film forming composition may be from about 12 weight % to about 14 weight %, or about 13 weight %.

Fatty Acids

The oral care product or the film forming composition thereof may optionally include one or more fatty acids configured to serve as a plasticizer and/or improve durability of the film formed from the film forming composition. Illustrative fatty acids may be or include, but are not limited to, one or more food grade fatty acids, such as, for example, stearic acid and oleic acid. Illustrative oleic acids may include EMERSOL® oleic acid, commercially available from DeWolf Chemical of Warwick, R.I., and PAMOLYN® oleic acid, commercially available from Eastman Chemical Company of Kingsport, Tenn. The fatty acids may be present in the oral care product or the film forming composition thereof in an amount from about 0.01 weight % to about 2 weight %, based on a total weight of the oral care product or the film forming composition thereof.

Adhesive or Adhesion Enhancing Agent

In at least one implementation, the oral care product or the film forming composition thereof may optionally include one or more adhesives configured to improve, maintain, and/or facilitate the adhesion of the film formed from the film forming composition to surfaces of the oral cavity. The one or more adhesives may also be configured to increase the hydrophobicity of the film formed from the film forming composition, thereby allowing the film to withstand external challenges, such as abrading, rubbing, or brushing.

Illustrative adhesives may be or include, but are not limited to, alkyd resins, polyvinyl acetaldehydes, polyvinyl alcohols, polyvinyl acetates, poly(ethylene oxide), polyacrylates, ketone resins, polyvinylpyrolidone, polyvinylpyrolidone/vinyl acetate copolymer, polyethylene glycols of 200 to 1000 molecular weight, polyoxyethylene/polyoxopropylene block copolymers (Polyox), silicon resins, or the like, and mixtures or combinations thereof. In at least one implementation, the one or more adhesives may include siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof. In at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin such that the polydiorganosiloxane is lightly cross-linked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents are available under the trade name BIO-PSA from the Dow Corning Company of Midland, Mich. The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), and 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, Mich.

In some embodiments, the adhesive is a natural resin. Illustrative natural resins may be or include, but are not limited to, shellac, rosins, or the like, and mixtures or combinations thereof. Shellac is commercially available and may be provided with a solvent (e.g. ethanol). One such commercially available shellac, known as Refined Pharmaceutical Glaze, is available from Mantrose-Haeuser Co., Inc. of Westport, Conn. The adhesive may also be or include any one or more of the rosins disclosed herein.

The amount or concentration of the adhesion enhancing agents present in the oral care product or the film forming composition thereof may vary widely. The amount of the adhesion enhancing agents present in the film forming composition may be from about 1 weight % to about 5 weight %. For example, the amount of the adhesion enhancing agents present in the film forming composition may be from about 1.0 weight %, about 1.5 weight %, about 2.0 weight %, about 2.5 weight %, or about 3.0 weight % to about 3.5 weight %, about 4.0 weight %, about 4.5 weight %, or about 5.0 weight %. In another example, the amount of the adhesion enhancing agents present in the film forming composition may be from about 1.0 weight % to about 5.0 weight %, about 1.5 weight % to about 4.5 weight %, about 2.0 weight % to about 4.0 weight %, or about 2.5 weight % to about 3.5 weight %. In yet another example, the amount of the adhesion enhancing agents present in the film forming composition may be greater than or equal to greater than or equal to 1.0 weight %, greater than or equal to 1.5 weight %, greater than or equal to 2.0 weight %, greater than or equal to 2.5 weight %, greater than or equal to 3.0 weight %, greater than or equal to 3.5 weight %, greater than or equal to 4.0 weight %, or greater than or equal to 4.5 weight %. In another example, the amount of the adhesion enhancing agents present in the film forming composition may be less than or equal to 1.0 weight %, less than or equal to 1.5 weight %, less than or equal to 2.0 weight %, less than or equal to 2.5 weight %, less than or equal to 3.0 weight %, less than or equal to 3.5 weight %, less than or equal to 4.0 weight %, less than or equal to 4.5 weight %, or less than or equal to 5.0 weight %. In a typical implementation, the amount of the adhesion enhancing agents present in the film forming composition is about 3.0 weight %.

Thickening System

In at least one implementation, the oral care product or the film forming composition thereof may optionally include a thickening system having one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. The thickening system may include a cross-linked polyvinylpyrrolidone (PVP) polymer. The thickening system may also include POLYPLASDONE® XL 10F, which is commercially available from Ashland Inc. of Covington, Ky. Additional illustrative thickeners may include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, hydrophilic polymers, such as carbomers, such as carboxymethylene polymers, such as acrylic acid polymers, and acrylic acid copolymers, and the like, and mixtures or combinations thereof. Carboxypolymethylene is a slightly acidic vinyl polymer with active carboxyl groups. One such carboxypolymethylene is CARBOPOL® 974 and/or 980, commercially available from Noveon, Inc. of Cleveland, Ohio. In at least one implementation, the one or more thickeners may be or include a cellulose ether, selected from one or more of hydroxyalkyl cellulose polymers, such as hydroxypropyl methyl cellulose (HPMC), hydroxypropyl cellulose, hyrdoxyethyl cellulose, methyl cellulose, ethylcellulose, carboxymethyl cellulose, and mixtures or combinations thereof.

In at least one implementation, the thickening system may include a single thickener. For example, the thickening system may include the cross-linked polyvinylpyrrolidone (PVP) polymer. In another implementation, the thickening system may include a plurality of thickeners. For example, the thickening system may include the cross-linked PVP polymer and a silica thickener. In another example, the thickening system may include a plurality of silica thickeners.

The amount or concentration of the thickening system and/or the thickeners thereof present in the oral care product or the film forming composition thereof may vary widely. The amount of the thickening system and/or the thickeners thereof present in the oral care product or the film forming composition thereof may be from about 10 wt % to about 30 wt % based on the total weight of the oral care product or the film forming composition thereof. For example, the amount of the thickening system and/or the thickeners thereof present in the oral care product or the film forming composition thereof may be from about 10 wt %, about 11 wt %, about 12 wt %, about 13 wt %, about 14 wt %, about 15 wt %, about 16 wt %, about 17 wt %, about 18 wt %, about 19 wt %, about 20 wt %, or about 21 wt % to about 22 wt %, about 23 wt %, about 24 wt %, about 25 wt %, about 26 wt %, about 27 wt %, about 28 wt %, about 29 wt %, or about 30 wt %. In another example, the amount of the thickening system and/or the thickeners thereof present in the oral care product or the film forming composition thereof may be from about 12 wt % to about 30 wt %, about 13 wt % to about 29 wt %, about 14 wt % to about 28 wt %, about 15 wt % to about 27 wt %, about 16 wt % to about 26 wt %, about 17 wt % to about 25 wt %, about 18 wt % to about 24 wt %, about 19 wt % to about 23 wt %, or about 20 wt % to about 22 wt %. In a typical implementation, the amount of the thickening system and/or the thickeners thereof present in the oral care product or the film forming composition thereof may be from about 20 wt % to about 22 wt %, more typically about 21 wt %.

Flavoring Agents

The film forming composition may also include one or more flavoring agents. Illustrative flavoring agents that may be utilized in the film forming composition may be or include, but are not limited to, essential oils and various flavoring aldehydes, esters, alcohols, and similar materials, as well as sweeteners such as sodium saccharin, and the like, and mixtures or combinations thereof. Illustrative essential oils may include, but are not limited to, oils of spearmint, peppermint, wintergreen, sassafras, clove, sage, eucalyptus, marjoram, cinnamon, lemon, lime, grapefruit, and orange. Also useful are chemicals such as menthol, carvone, anethole, and the like, and mixtures or combinations thereof. In a preferred implementation, the flavoring agents include oils of peppermint and spearmint.

The amount or concentration of the one or more flavoring agents present in the oral care product or the film forming composition thereof may vary widely. In at least one implementation, the amount of the one or more flavoring agents present may be from about 0.01 weight % to about 50 weight %, based on a total weight of the oral care product or the film forming composition thereof. For example, the amount of the one or more flavoring agents present may be from about 0.01 weight %, about 1 weight %, about 5 weight %, about 10 weight %, about 15 weight %, about 20 weight %, or about 25 weight % to about 30 weight %, about 35 weight %, about 40 weight %, about 45 weight %, or about 50 weight %.

Orally Acceptable Vehicle

In at least one implementation, the film forming composition may be dispersed or dissolved in an orally acceptable vehicle. As used herein, the expression "orally acceptable vehicle" may refer to a suitable vehicle, ingredient, or combination of ingredients, which can be used to form and/or apply the film forming composition or one or more components thereof to surfaces of the oral cavity in a safe and effective manner. For example, the orally acceptable vehicle may be a suitable solvent, and the film forming composition may be dispersed, dissolved, mixed, or otherwise contacted with the suitable solvent to prepare or form the oral care product. Illustrative solvents may be or include, but are not limited to, ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, or the like, and mixtures or combinations thereof. In a preferred implementation, the orally acceptable vehicle is ethanol.

It should be appreciated that the orally acceptable vehicle may include materials such as, but not limited to, one or more antibacterial agents, anticalculus agents, buffers, sources of peroxide (e.g., hydrogen peroxide), alkali metal bicarbonate salts, thickening materials, humectants, water, surfactants, titanium dioxide, cooling agents, coloring agents, and the like, and combinations thereof. In at least one implementation, the film forming composition or the orally acceptable vehicle thereof may exclude any of the aforementioned materials. For example, the film forming composition or the orally acceptable vehicle thereof may exclude titanium dioxide (e.g., titanium dioxide particles for aiding and facilitating occlusion of dentin tubules).

The orally acceptable vehicle may make up the balance of the oral care product. In at least one implementation, the orally acceptable vehicle (e.g., ethanol) may be present in an amount of at least 60 weight %, at least 62 weight %, at least 64 weight %, at least 66 weight %, at least 68 weight %, at least 70 weight %, at least 72 weight %, at least 74 weight %, at least 76 weight %, at least 78 weight %, at least 80 weight %, at least 82 weight %, at least 84 weight %, at least 86 weight %, at least 88 weight %, at least 90 weight %, at least 92 weight %, at least 94 weight %, at least 96 weight %, at least 98 weight %, or at least 99 weight %, based on a total weight of the oral care product.

Additional Ingredients

It should be appreciated by one having ordinary skill in the art, that the oral care products and/or the film forming compositions thereof may include other additional ingredients/components. For example, the oral care products and/or the film forming compositions thereof may include desensitizing agents, viscosity modifiers, diluents, surface active agents (e.g., emulsifiers, foam modulators, etc.), pH modifying agents (e.g., acids and bases), humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

All ingredients for use in the compositions described herein should be orally acceptable. As used herein, "orally acceptable" may refer to any ingredient that is present in a composition as described in an amount and form that does not render the composition unsafe for use in the oral cavity.

Methods

The present disclosure may provide methods for reducing dental sensitivity of teeth in a human or animal subject in need thereof, and methods for at least partially occluding dentin tubules of teeth in human or animal subjects in need thereof. As used herein "animal subject" may include higher order non-human mammals such as canines, felines, and horses. The method may include contacting any one of the film forming compositions disclosed herein with surfaces of the oral cavity, such as surfaces of teeth. Contacting the surface of the teeth with the film forming composition may include applying the film forming composition directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, spray, roller ball, or non-woven pad, or the like. Contacting the surface of the teeth with the film forming composition may also include disposing the film forming composition in a dental tray (e.g., reservoir of a dental tray) and disposing the dental tray about the teeth.

The method may also include evaporating a solvent or orally acceptable vehicle from the film forming composition to form a film on the surfaces of the teeth. The resulting film, formed in situ, may at least partially occlude dentin tubules of the teeth to at least partially reduce sensitivity of the teeth. The method may also include maintaining the film on the surfaces of the teeth for at least 12 hours, at least one day, at least two days, at least three days, at least four days, or more.

The method may also include applying the film forming composition to surfaces of the teeth during or after treatment with a toothpaste, such as a toothpaste for treating sensitive teeth (e.g., Colgate® Sensitive Pro-Relief™).

The method may include applying or contacting the oral care product and/or the film forming composition thereof with the surfaces of the teeth at predetermined intervals. For example, the method may include applying or contacting the oral care product and/or the film forming composition thereof with the surfaces of the teeth after brushing, on a daily basis, every other day, once or twice a week, or once a month. In another example, the method may include applying or contacting the oral care product and/or the film forming composition thereof with the surfaces of the teeth at least once a day, at least once every two days, at least once every three days, at least once every five days, at least once a week, at least once every two weeks, or at least once a month. The oral care product and/or the film forming composition thereof may be utilized for up to 2 weeks, up to 3 weeks, up to 4 weeks, up to 6 weeks, up to 8 weeks, or greater.

The present disclosure may further provide methods for preparing a film forming composition. The method may include mixing, dissolving, combining, or otherwise contacting each component of the film forming composition with one another. For example, the method may include contacting an acrylate/octylacrylamide copolymer, a rosin (e.g., a hydrogenated rosin), an orally acceptable vehicle or solvent, a cellulose derivative, and/or a fatty acid with one another. The components or ingredients of the film forming composition may be homogenized via any acceptable mixing technique or method.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of exemplary film forming compositions (1)-(3) for reducing sensitivity was evaluated in vitro. Particularly, the efficacy of the film forming compositions (1)-(3) for plugging or occluding dentin tubules was evaluated. The test or exemplary film forming compositions (1)-(3) were prepared by combining the ingredients/components according to Table 1. Particularly, the ingredients/components of each of the test film forming (1)-(3) were combined or otherwise contacted with one another in a spin mix jar and mixed at about 3540 rpms for about 5 minutes or until a homogenous suspension was obtained.

TABLE 1

Test Film Forming Compositions (1)-(3)

| INGREDIENT/COMPONENT | (1) wt % | (2) wt % | (3) wt % |
| --- | --- | --- | --- |
| Acrylates/Octylacrylamide Copolymer | 20.0 | 20.0 | 15% |
| Ethylcellulose | 0.8 | 0.8 | — |
| Hydrogenated Rosin | 5.0 | 5.0 | — |
| Titanium Dioxide | 1.5 | — | — |
| Fatty Acids | 1.0 | 1.0 | — |
| Arginine | — | — | 1.5% |
| PCC | — | — | 1.5% |
| Fumed Silica | — | — | 2.8% |
| Ethanol | 71.7 | 73.2 | 79.2% |
| Total | 100 | 100 | 100% |

Human molars were sliced and polished to prepare dentin slices. To evaluate the efficacy of the film forming compositions (1)-(3), each of the film forming compositions was applied directly to dry dentin surfaces of respective human dentin slices with a soft, nail polish type of brush. These were left at room temperature for 15 minutes, and then placed in a PBS solution for an additional 15 minutes. At the end of the 15 minutes, the film that was formed on the dentin surfaces was removed, and the procedure was repeated five times. Confocal images of the dentin slices (five per slice) were taken prior to treatment with the respective film forming compositions (1)-(3) to provide a baseline. Similarly, confocal images of the human dentin slides (five per slice) were taken after treatment to evaluate the ability of each of the film forming compositions (1)-(3) for occluding the dentin tubules. The results are summarized in Table 2.

TABLE 2

Percentage of Dentin Occlusion for Test Composition (1)-(3)

| | Test Composition (1) | Test Composition (2) | Test Composition (3) |
| --- | --- | --- | --- |
| After Treatment | 40.2% | 43.6% | 72.4% |
| After Coke/Acid Challenge | — | — | 69.0% |

As illustrated in Table 2, each of the test film forming compositions (1)-(3) provided significant occlusion of the dentin tubules. Specifically, the first and second film forming compositions (1) and (2) provided 40.20% and 43.60% occlusion of the dentin tubules, respectively. It was surprisingly and unexpectedly discovered that the film forming composition that did not include titanium dioxide, which is properly sized to aid or facilitate in the occlusion of the dentin tubules, exhibited relatively increased occlusion of the tubules, as compared to the test composition (1) including the titanium dioxide. The film forming composition (3) containing arginine/PCC provided the best occlusion result. The polymer coating was able to deliver arginine/PCC into dentine tubules and block the tubules. More surprisingly and unexpectedly, the polymer was able to protect the blocked dentine tubules from coke/acid challenge and provided a longer lasting sensitivity relief benefit than toothpaste (See Table 3). These results demonstrated the ability of the film forming compositions (1)-(3) for reducing sensitivity and/or occlude dentin tubules.

Example 2

The efficacy of the exemplary film forming composition (1) of Example 1 for maintaining, facilitating, and/or enhancing the occlusion of dentin tubules in conjunction with a commercial toothpaste for sensitivity (i.e., Colgate® Sensitive Pro-Relief™) was evaluated on dentin slices. The study was conducted by preparing a slurry of the commercial toothpaste and a phosphate buffered saline (PBS) in a 3:1 ratio. The slurry was applied to the dentin surface by brushing with a soft, nail polish type of brush for 30 seconds, followed by 15 minutes of PBS treatment. This procedure was repeated five times. Half of the dentin slices received a one-time treatment with the exemplary film forming composition (1), and the other half did not. After treatment, all of the human dentin slices were challenged with an acid (i.e., Coca Cola®) for one minute. Confocal images were taken prior to any treatment (baseline), after treatment with the commercial toothpaste the exemplary film forming composition (1), and after the acid challenge. The results are summarized in Table 3.

TABLE 3

Percentage of Dentin Occlusion

| | Commercial Sensitive Toothpaste | Sensitive Toothpaste + Test Composition (1) |
|---|---|---|
| After Treatment | 65.70% | 67.70% |
| After Coke/Acid Challenge | 32.80% | 66.20% |

As illustrated in Table 3, applying the film forming composition (1) to the teeth after treatment with a commercial toothpaste, intended to provide sensitivity relief by dentin tubule occlusion, surprisingly allowed the teeth to maintain the high percentage of dentin occlusions after challenging with an acid.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A film forming composition for occluding dentin tubules of teeth, the film forming composition comprising:
   a hydrophobic copolymer;
   one or more desensitizing agents; and
   an orally acceptable volatile solvent,
wherein the hydrophobic copolymer comprises an acrylate/octylacrylamide copolymer, wherein the composition does not contain an alkyl cellulose ether, and wherein the composition does not contain an adhesive.

2. The film forming composition of claim 1, wherein the desensitizing agents comprise at least one of a potassium salt, arginine, participated calcium carbonate, small particle silica, eugenol, strontium salts, zinc salts, chloride salts, or combinations thereof.

3. The film forming composition of claim 1, wherein the orally acceptable solvent comprises one or more of ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, and benzyl alcohol.

4. The film forming composition of claim 1, further comprising one or more fatty acids, optionally, the fatty acids is oleic acid.

5. The composition of claim 1, wherein the hydrophobic copolymer is present in an amount of from 10% to 30% by weight of the composition.

6. The composition of claim 3, wherein the orally acceptable solvent comprises ethanol.

7. The composition of claim 2, wherein the desensitizing agents comprise arginine.

8. A film forming composition for occluding dentin tubules of teeth, the film forming composition consisting of:
   one or more acrylate/octylacrylamide copolymers;
   one or more desensitizing agents; and
   one or more orally acceptable volatile solvents.

9. The film forming composition of claim 8 wherein
   the one or more desensitizing agents comprise arginine, participated calcium carbonate, and small particle silica; and
   the one or more orally acceptable solvents comprise ethanol.

10. A method for at least partially occluding dentin tubules of teeth in a subject, comprising contacting the film forming composition of claim 1 with the teeth of the subject in need thereof.

11. A method for treating or reducing dental sensitivity of teeth of a subject, comprising applying the film forming composition of claim 1 with the teeth of the subject in need thereof.

12. The method of claim 11, further comprising treating the teeth with a toothpaste.

13. The method of claim 12, wherein the film forming composition is applied after treating the teeth with the toothpaste.

* * * * *

UNITED STATES PATENT AND TRADEMARK OFFICE
CERTIFICATE OF CORRECTION

PATENT NO. : 11,173,105 B2
APPLICATION NO. : 16/161162
DATED : November 16, 2021
INVENTOR(S) : Rong Dong et al.

It is certified that error appears in the above-identified patent and that said Letters Patent is hereby corrected as shown below:

In the Specification

In Column 1, Line 65, delete "participated" and insert -- precipitated --, therefor.

In the Claims

In Column 16, Line 5, in Claim 2, delete "participated" and insert -- precipitated --, therefor.

In Column 16, Line 33, in Claim 9, delete "participated" and insert -- precipitated --, therefor.

Signed and Sealed this
Twenty-first Day of March, 2023

Katherine Kelly Vidal
*Director of the United States Patent and Trademark Office*